US008100015B2

(12) United States Patent
Karasawa et al.

(10) Patent No.: US 8,100,015 B2
(45) Date of Patent: Jan. 24, 2012

(54) ULTRASONIC INSPECTION APPARATUS AND ULTRASONIC PROBE USED FOR SAME

(75) Inventors: Hirokazu Karasawa, Yokohama (JP); Hideo Isobe, Kawasaki (JP)

(73) Assignees: Kabushiki Kaisha Toshiba, Tokyo (JP); Toshiba Plant Systems & Service Corporation, Tokyo (JP)

( * ) Notice: Subject to any disclaimer, the term of this patent is extended or adjusted under 35 U.S.C. 154(b) by 800 days.

(21) Appl. No.: 11/943,444

(22) Filed: Nov. 20, 2007

(65) Prior Publication Data

US 2009/0126494 A1  May 21, 2009

(51) Int. Cl.
*G01N 29/265* (2006.01)
*G01N 29/06* (2006.01)

(52) U.S. Cl. ........................................... 73/602
(58) Field of Classification Search ............ 73/602
See application file for complete search history.

(56) References Cited

U.S. PATENT DOCUMENTS

| 6,532,820 | B1 * | 3/2003 | Fleming et al. | 73/627 |
| 2006/0219013 | A1 * | 10/2006 | Baba et al. | 73/618 |
| 2007/0006658 | A1 * | 1/2007 | Kennedy et al. | 73/622 |
| 2007/0282543 | A1 * | 12/2007 | Hiyama et al. | 702/39 |
| 2008/0245150 | A1 * | 10/2008 | Katayama et al. | 73/602 |

FOREIGN PATENT DOCUMENTS

| JP | 02-049156 | | 2/1990 |
| JP | 05-023332 | | 2/1993 |
| JP | 7-184903 | | 7/1995 |
| JP | 2002214204 A | * | 7/2002 |
| JP | 2003-149213 | | 5/2003 |
| JP | 2003260056 A | * | 9/2003 |
| JP | 2004-053360 | | 2/2004 |
| JP | 2005315582 A | * | 11/2005 |
| JP | 2006296464 A | * | 11/2006 |
| JP | 2006317417 A | * | 11/2006 |

* cited by examiner

*Primary Examiner* — Hezron E Williams
*Assistant Examiner* — Rose M Miller
(74) *Attorney, Agent, or Firm* — Finnegan, Henderson, Farabow, Garrett & Dunner, L.L.P.

(57) ABSTRACT

An ultrasonic inspection apparatus includes an ultrasonic probe including an ultrasonic transducer, a position detection device, a drive element selector which is connected to the plurality of piezoelectric elements of the ultrasonic transducer provided so as to select a required piezoelectric element, a signal detection circuit which allows the piezoelectric element selected by the drive element selector to transmit ultrasonic wave to an inspection object through an acoustic transmission medium, which receives reflection echo thereof, and which detects an electric signal of the reflection echo through, a signal processor which generates three-dimensional imaging data inside of the inspection object by processing the electric signal of the detected reflection echo, a position converting circuit which outputs an imaging-start trigger signal to a signal generator in response to a position detection signal, and a display device which displays an imaging result.

8 Claims, 5 Drawing Sheets

ULTRASONIC INSPECTION APPARATUS AND ULTRASONIC PROBE USED FOR SAME

BACKGROUND OF THE INVENTION

1. Field of the Invention

The present invention relates to a three-dimensional ultrasonic inspection technology for non-destructively inspecting an internal structure of an inspection object (object to be inspected), a defect state (defective) and a joined state by using ultrasonic wave, and more particularly, to a portable ultrasonic inspection apparatus and an ultrasonic probe used for the ultrasonic inspection apparatus for visualizing defect, exfoliation, void in an inspection object and a peel of the joined portion.

2. Related Art

As the ultrasonic inspection technique of this kind, there is known a three-dimensional ultrasonic inspection apparatus disclosed, for example, in Japanese Unexamined Patent Application Publication Nos. 2003-149213 (Patent Publication 1) and 2004-53360 (Patent Publication 2).

The three-dimensional ultrasonic inspection apparatus includes an ultrasonic transducer in which a large number of piezoelectric elements (piezoelectric elements) are arranged on a plane in a matrix or array (linear) arrangement. The three-dimensional ultrasonic inspection apparatus three-dimensionally visualizes an internal structure of an inspection object, or states of defect, void, oxide film, peel and the like by using ultrasonic wave which is transmitted from or received to the ultrasonic transducer to and from an inspection object, and inspects the inspection object non-destructively (in a non-destructive manner).

According to the three-dimensional ultrasonic inspection apparatus using the ultrasonic transducer having the many piezoelectric elements, it is possible to visualize a layer structure of an inspection object having a plurality of acoustic features, and states of defect, void, peel and the like in the inspection object by means of ultrasonic wave, but imaging results become nonuniform in accordance with transmitting and receiving patterns of ultrasonic wave in three-dimensional imaging data obtained by processing a received echo signal of the ultrasonic transducer, it becomes difficult to precisely and quantitatively determine whether quality of inspection object is excellent or not, and it is necessary to visually determine the inspection result. The results are varied due to differences among individuals.

A conventional ultrasonic inspection apparatus uses an ultrasonic transducer having a piezoelectric converter in which a large number of piezoelectric elements are disposed. However, when internal inspection of an inspection object is to be carried out while moving the ultrasonic transducer for scanning, the ultrasonic inspection apparatus does not have a moving amount detection device for detecting a moving amount of the ultrasonic transducer, and in order to detect a moving amount of the ultrasonic transducer, it is necessary to separately and independently provide a large-scale moving amount detection device such as an X-Y table having a position detector therein.

Therefore, it is difficult to make the ultrasonic inspection apparatus portable and to effectively and precisely inspect an internal state of an inspection object by using ultrasonic wave at a field or site of manufacturing procedure.

Even when the ultrasonic inspection apparatus is provided with the large-scale moving amount detection device such as the X-Y table, there is a limitation in a scanning range of the ultrasonic transducer in which the piezoelectric elements are arranged in the form of a matrix or array, and if the inspection object has a curved shape or a large portion having a wide area, it is difficult to efficiently and effectively inspect the inspection object by using ultrasonic wave.

SUMMARY OF THE INVENTION

The present invention has been accomplished in view of the above-described circumferences, and it is an object of the present invention to provide a portable ultrasonic inspection apparatus and an ultrasonic probe used for the ultrasonic inspection apparatus in which the ultrasonic probe can easily and manually scan an inspection object at a field or a site of manufacturing procedure, and an inside defect, exfoliation and void in the inspection object, and peel of a joined portion can efficiently and precisely be inspected.

It is another object of the present invention to provide an ultrasonic inspection apparatus and an ultrasonic probe used for the ultrasonic inspection apparatus in which the ultrasonic probe is separated from an apparatus body and the ultrasonic inspection apparatus and the ultrasonic probe can be made compact and portable.

It is another object of the present invention to provide an ultrasonic probe in which the probe is integrally provided with a position detection device which detects a moving amount and a moving direction, the probe is easily and efficiently manually operated at a field or a site of manufacturing procedure, and interior of an inspection object can efficiently and precisely be inspected.

The above and other objects can be achieved according to the present invention by providing, in one aspect, an ultrasonic inspection apparatus comprising:

an ultrasonic probe provided with an ultrasonic transducer including a plurality of piezoelectric elements and a position detection device;

a drive element selector which is connected to the plurality of piezoelectric elements of the ultrasonic transducer provided and which selects a required piezoelectric element;

a signal generator generating a drive signal for selecting the required piezoelectric element;

a signal detection circuit which allows the piezoelectric element to transmit an ultrasonic wave to an inspection object through an acoustic transmission medium, which receives a reflection echo of the ultrasonic wave and which detects an electric signal of the reflection echo;

a signal processor generating three-dimensional imaging data inside of the inspection object by processing the electric signal of the detected reflection echo through a parallel arithmetic processing;

a position converting circuit configured to output an imaging-start trigger signal to the signal generator in response to a position detection signal detected by the position detection device; and a display device displaying an imaging result in which a position signal of the ultrasonic transducer taken from the position converting circuit and a plurality of image data sets taken from the signal processor are integrally coupled to each other.

In this aspect, it may be desired that the ultrasonic probe is connected to an apparatus body of the ultrasonic inspection apparatus through a flexible signal cable, and the ultrasonic probe is integrally assembled with an ultrasonic transducer and a non-contact optical position detection device in a probe holder.

The optical position detecting device may include a pair of optical position detecting units, and each optical position detecting units includes a light source which visualizes a surface of the inspection object, a light receiving section which receives a light reflected from the surface of the inspection object of an illumination light radiated from the light source, and a position detector which outputs a position detection signal detected by the light receiving section to the position converting circuit generating an imaging-start trigger signal.

It may be also desired that the ultrasonic probe is connected to an apparatus body of the ultrasonic inspection apparatus, and the ultrasonic probe is integrally assembled with an ultrasonic transducer and a mechanical position detection device in a probe holder.

The mechanical position detection device may be provided on one side surface on the side of the ultrasonic transducer or two side surfaces which intersect with each other at right angles. The mechanical position detection device may be integrally provided on a side of the ultrasonic transducer, and the mechanical position detection device includes a wheel rolling on the surface of the inspection object and an encoder detecting a rotation amount of the wheel.

In another aspect of the present invention, there is also provided an ultrasonic probe connected to an ultrasonic inspection apparatus through a flexible signal cable, comprising a box-shaped probe holder;

an ultrasonic transducer including a plurality of piezoelectric elements incorporated in the probe holder; and a position detection device integrally provided with the ultrasonic transducer and configured to detect the position thereof, the ultrasonic transducer and the position detection device being integrally assembled in the probe holder.

In this aspect, it may be desired that the position detection device has an optical structure including at least a pair of optical position detectors, and the optical position detecting device is held in a non-contact state with respect to a surface of an inspection object when the probe holder is placed on the surface thereof. The optical position detecting device may include at least a pair of optical position detectors, each of which includes a light source which visualizes a surface of an inspection object, a light receiving section which detects a reflection light of an illumination light transmitted from the light source, and a position detector which outputs a position detection signal detected by the light receiving section to a position converting circuit.

The position detection device may be a mechanical position detection device provided on one side surface of the ultrasonic transducer or two side surfaces thereof which intersect with each other at right angles. The mechanical position detection device may be integrally provided on the ultrasonic transducer, and the mechanical position detection device includes a wheel rolling on a surface of an inspection object and an encoder detecting a rotation amount of the wheel.

In the ultrasonic inspection apparatus and the ultrasonic probe device for the ultrasonic inspection apparatus according to the present invention of the characters mentioned above, the ultrasonic probe is connected to the apparatus body of the ultrasonic inspection apparatus through the flexible signal cable, and the ultrasonic probe is integrally assembled with the ultrasonic transducer and the optical or mechanical position detection device in the probe holder. Therefore, it is possible to easily and efficiently carry out the ultrasonic flaw inspection at a field or a site of manufacturing procedure only by manually scanning the ultrasonic probe on a surface of an object to be inspected.

The nature and further characteristic features of the present invention will be made clearer from the following descriptions made with reference to the accompanying drawings.

DESCRIPTION OF THE PREFERRED EMBODIMENT

Embodiments of the present invention will be explained hereunder with reference to the accompanying drawings.

Figure 1:
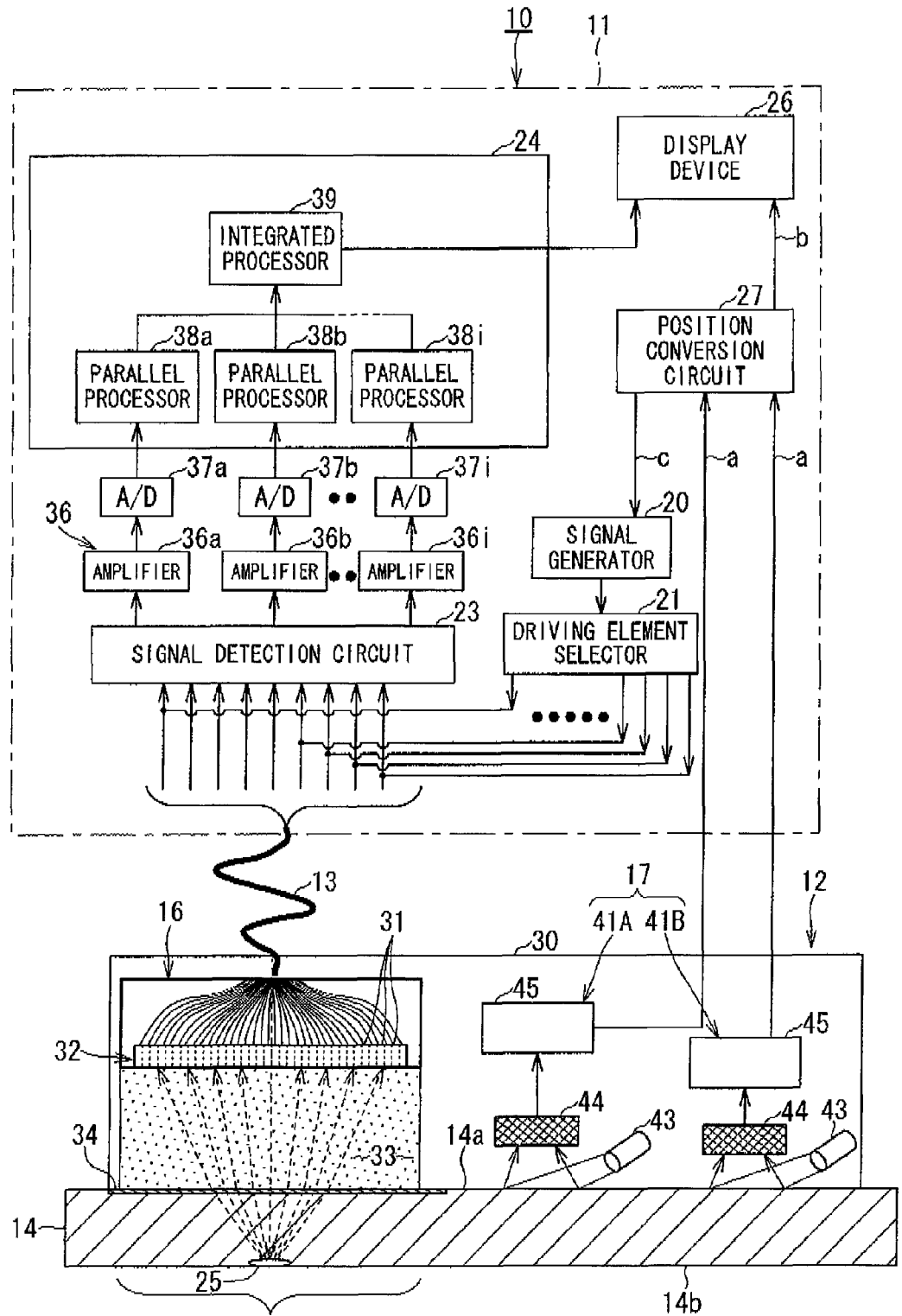
FIG. 1 is a block diagram showing a first embodiment of an ultrasonic inspection apparatus of the present invention.

With reference to FIG. 1 showing a first embodiment of an ultrasonic inspection apparatus according to the present invention, an ultrasonic inspection apparatus 10 is portable, an apparatus body 11 and a palm-size ultrasonic probe or probe unit 12 are separated in the ultrasonic inspection apparatus 10, and the ultrasonic probe 12 is connected to the apparatus body 11 through a flexible signal cable 13 such as an optical fiber cable.

The ultrasonic inspection apparatus 10 functions as a portable ultrasonic camera capable of precisely three-dimensionally imaging an internal structure of a defect shape (shape of defective) of an inspection object (object to be inspected) 14. The weight of the apparatus and its portable feature will be explained exemplarily.

The weight of the ultrasonic inspection apparatus 10 is 10 kg or less, preferably 7 kg or less. The ultrasonic probe 12 is of palm-size, and the weight thereof is 1 kg or less, more specifically, a few hundred g. The ultrasonic inspection apparatus 10 can be carried in a manner such that the apparatus body 11 is hung from a shoulder, put on a back or held. The ultrasonic probe 12 has a size, a shape and a weight capable, for an inspector, of manually gripping and scanning.

The ultrasonic inspection apparatus 10 includes an ultrasonic probe (unit) 12 integrally provided with an ultrasonic transducer 16 and an optical position detector 17, a signal generator 20 which generates a drive signal for driving the ultrasonic transducer 16, a drive element selector 21 for selecting the drive signal from the signal generator 20 to selectively drive piezoelectric elements of the ultrasonic transducer 16, a signal detection circuit 23 for irradiating an inspection region 22 of the inspection object 14 with ultrasonic wave transmitted from the ultrasonic transducer 16 to detect an electric signal of reflection echo from the inspection region 22 through the ultrasonic transducer 16, a signal processor 24 which subjects an electric signal of reflection echo detected by the signal detection circuit 23 to parallel arithmetic processing so as to generate three-dimensional (3D) ultrasonic wave image data, and display device 26 which carries out correction processing and comparison processing for three-dimensional ultrasonic imaging data and display image which are processed by the signal processor 24, and which automatically and precisely determines a state of an internal defect 25 of the inspection object 14 and display a determination result.

The ultrasonic inspection apparatus 10 can swiftly capture an internal structure of the inspection object 14 as high sensitive and high resolution three-dimensional ultrasonic wave image and can display the same, thus enabling high-speed inspection per one image at one to several tens seconds.

The three-dimensional ultrasonic inspection apparatus 10 may be applied to a maintenance state of welded portions, flaw concerning presence or absence of welding defect in automobile industries, aircraft industries and railroad industries, as well as state observation of welded portions of in plant industries and shipbuilding industries.

According to this ultrasonic inspection apparatus 10, the signal generator 20, the drive element selector 21, the signal detection circuit 23, the signal processor 24 and the display device 26 are provided in the apparatus body 11. The apparatus body 11 includes a position converting circuit 27 which is operated in association with the optical position detector 17 of the ultrasonic probe 12. The position converting circuit 27 may be incorporated in a probe holder 30 of the ultrasonic probe 12, and may constitute the ultrasonic probe 12 together with the ultrasonic transducer 16 and the optical position detector 17.

The position converting circuit 27 captures a position detection signal "a" from the optical position detector 17 of the ultrasonic probe 12, and subjects the position detection signal "a" to a conversion processing and then outputs the position conversion signal "b" to the display device 26. The position converting circuit 27 generates a trigger signal "c" for starting an imaging operation in the signal generator 20 whenever the moving amount is varied by a predetermined value, and then outputs the same.

The ultrasonic probe 12 includes the ultrasonic transducer 16 which transmits and receives ultrasonic wave, and the optical position detector 17 which simultaneously detects a moving direction, a moving distance and an inclination with respect to the moving direction of the ultrasonic transducer 16. The ultrasonic transducer 16 and the optical position detector 17 are integrally provided in the probe holder 30.

The ultrasonic transducer 16 includes a piezoelectric converter 32 in which a large number of piezoelectric elements 31 are arranged in a matrix form with "m" rows and "n" columns. The piezoelectric converter 32 constitutes a matrix transducer.

The ultrasonic inspection apparatus 10 functions as an ultrasonic camera having an ultrasonic transducer. The ultrasonic inspection apparatus 10 can instantaneously collect several thousand to several tens of thousand ultrasonic wave waveforms of reflection echo, and can subject the internal defect 25 (a state of a joined (junction) region, presence or absence of welding defect and a state of the welding defect) to imaging parallel arithmetic processing at a high speed.

Drive signals generated by the signal generator 20 are selected by the drive element selector 21 and added to each piezoelectric element 31 of the ultrasonic transducer 11. One or more driving orders of the piezoelectric elements 31 are determined by the selection of the drive element selector 21, and the piezoelectric elements 31 are driven at necessary driving timing. The piezoelectric elements 31 may be arranged on one line or on cross lines (array) instead of in the matrix form, and an array transducer may be constituted. The ultrasonic transducer 16 may be a matrix array or a linear array type transducer.

A transmitting/receiving surface which is a sensor surface of ultrasonic wave, more specifically, a liquid or a solid shoe member 33 which is acoustic transmission medium, is in intimate contact with the ultrasonic transducer 16 on the side of the inspection object 14. A couplant 34 which acoustically harmonizes ultrasonic wave is provided between a shoe member 33 and the inspection object 14. The couplant 34 is made of gel liquid having low volatility. When the shoe member 33 of the acoustic transmission medium is liquid, the couplant 34 is not necessary.

The shoe member 33 has an entirely box-like shape, and its opening area is formed in accordance with a size of an inspection region (target region) 22 of the inspection object 14. The height of the shoe member 33, which is the acoustic transmission medium, is determined by an oscillation angle (spreading angle) of the ultrasonic wave transmitted from the piezoelectric element 31.

The inspection region 22 of the inspection object 14 is internally inspected by the ultrasonic inspection apparatus 10 in a non-destructive manner using ultrasonic wave. A multi-layered structure in which two or more plate structures are superposed and welded on one another may be used. The inspection object 14 may be made of metal or resin.

The signal generator 20 applies a drive signal to the ultrasonic transducer 16. The signal generator 20 generates pulse or continuous drive signals by applying external voltage to thereby drive the piezoelectric substance of the piezoelectric element 31 so as to generate ultrasonic wave. If the drive element selector drives the piezoelectric converter 32, and the piezoelectric element 31 on m-th row and n-th column is selected, a drive signal is applied to the m-th row and n-th column piezoelectric element 31 at a necessary timing. The drive element selector 21 sequentially selects one or more piezoelectric elements 31 to be driven at a necessary timing, and if a drive signal from the signal generator 20 is applied to the selected piezoelectric element 31, the drive element selector 21 transmits ultrasonic wave U toward the inspection object 14 from the piezoelectric element 31.

The ultrasonic wave sequentially transmitted from the piezoelectric elements 31 of the ultrasonic transducer 16 passes through the shoe member 33 as an acoustic radio wave medium, transmitted into the inspection region 22 of the inspection object 14 through the couplant 34. The ultrasonic wave is then reflected by boundary layers in the inspection region 22.

The reflection echo of ultrasonic wave reflected by boundary layers such as a surface 14a, a boundary surface, a bottom surface 14b of the inspection object 14 and a defect 25 is received by the piezoelectric elements 31 of the ultrasonic transducer 16 through the acoustic transmission medium 31 from the inspection object 14. The reflection echo vibrates the piezoelectric elements 31 and is converted into an electric signal of reflection echo. The electric signal of the reflection echo is inputted to the signal detection circuit 23, and as a result of the above process, the electric signal of the reflection echo is detected for each piezoelectric element 31.

If a drive signal is applied to the m-th row and n-th column piezoelectric element 31 among the piezoelectric elements 31 of the ultrasonic transducer 16, the piezoelectric element 31 is operated and ultrasonic wave as piezoelectric substance is generated, and the three-dimensional ultrasonic inspection apparatus 10 generates the ultrasonic wave U. The generated ultrasonic wave U is transmitted to the inspection region 22 of the inspection object 14 through an acoustic transmission medium 32 and a couplant 33.

A portion of the ultrasonic wave U transmitted to the inspection region 22 of the inspection object 14 is reflected from the density boundary layer of the inspection region 22 and becomes reflection echo. The reflection echo is returned to a matrix transducer (ultrasonic transducer) 16 through the couplant 33 and the acoustic transmission medium 32, and is received by the piezoelectric elements 31 with time lag. The reflection echo becomes an electric signal by piezoelectric conversion by the piezoelectric element 31 and is sent to the signal detection circuit 23 through a signal cable 13 and detected.

The ultrasonic transducer 16 sequentially and selectively applies a drive signal to the piezoelectric elements 31 by the drive element selector 21. The piezoelectric elements 31 are sequentially driven at a necessary timing, and the ultrasonic transducer 16 two-dimensionally receives reflection echo of ultrasonic wave transmitted from the piezoelectric elements 31 by an ultrasonic transducer 16.

Here, if "m" rows and "n" columns of the piezoelectric elements 31 are 10×10 (100) piezoelectric elements 31 are arranged on a plane (two dimension) in a matrix form, and the piezoelectric elements 31 are sequentially driven by the drive element selector 21. If the drive signals are sequentially applied to the piezoelectric elements 31, ultrasonic wave is sequentially transmitted from the piezoelectric elements 31 at the driving timing.

Ultrasonic wave reflection echo sequentially transmitted from the piezoelectric elements 22 are sequentially received by the ultrasonic transducer 16, and an electric signal of the reflection echo which is the reception signal is sent to the signal detection circuit 23 through the signal cable 13.

The signal detection circuit 23 is connected to the piezoelectric elements 31 of the ultrasonic transducer (ultrasonic sensor) 16 through the signal cable 13 in a well-ordered manner, and electric echo signal generated in each piezoelectric element 31 of the piezoelectric converter 32 is introduced into the signal detection circuit 23 through the signal cable 13. A drive signal from the signal generator 20 is introduced into each piezoelectric element 31 of the piezoelectric converter 32 through the drive element selector 21 utilizing the signal cable 13.

The reflection echo received by the piezoelectric converter 32 of the ultrasonic transducer 16 is converted into an electric signal by the piezoelectric converter 32 and becomes an electric echo signal and is sent to the signal detection circuit 23. The signal detection circuit 23 detects an electric signal of reflection echo generated in the ultrasonic transducer 16.

Among the electric echo signals detected by the signal detection circuit 23, a plurality of electric echo signals required for the inspection are introduced into amplifiers 36a, 36b, . . . 36i constituting an amplifier circuit 36.

The amplifiers 36a, 36b, . . . 36i amplify the introduced electric echo signals and supply the same to A/D converters 37a, 37b, . . . 37i. The A/D converters 37a, 37b, . . . 37i A/D convert analog signals of the amplified electric echo signals into digital signals, and introduce the same to parallel processors 38a, 38b, . . . 38i of the signal processor 24 as drive element selectors.

The signal processor 24 includes the plurality of parallel processors 38a, 38b, . . . 38i, and an integrated processor 39 which integrates a plurality of image information sets generated by the parallel processors 38a, 38b, . . . 38i.

The parallel processors 38a, 38b, . . . 38i of the signal processor 24 process drive element selectors introduced from the A/D converters 37a, 37b, . . . 37i, and generate image information for visualizing an internal state of the inspection object 14.

The plurality of image information sets generated by the parallel processors 38a, 38b, . . . 38i are integrated by the integrated processor 39 into one and is introduced to the display device 26.

When the signal detection circuit 23 or the signal processor 24 is provided with a multiplexer, not shown, the plurality of parallel processors 38a, 38b, . . . 38i and the integrated processor 39 become unnecessary, and one parallel processor can form the integrated image information.

The ultrasonic wave echo signal, which is digitalized by the signal processor 24, is processed, and the three-dimensional ultrasonic wave image information is generated. The three-dimensional ultrasonic wave image information is sent to the display device 26, which is then displayed on the display device 26.

The ultrasonic probe 12 is integrally provided with the ultrasonic transducer 16 and the optical position detection device 17 in the probe holder 30. The optical position detection device 17 is a non-contact position detector which detects moving distances (moving amounts) of the ultrasonic probe 12 and the ultrasonic transducer 16 and the inclinations thereof with respect to the moving directions.

The optical position detection device 17 includes a pair of optical position detection means 41A and 41B. The optical position detection means 41A and 41B are disposed at a given distance (known distance) from each other in a state where they are mechanically coupled to each other so as to integrally move with respect to the ultrasonic transducer 16. The pair of optical position detection means 41A and 41B have the same structures and functions. The pair of optical position detection means 41A and 41B are disposed adjacently as shown in the drawing, but it may be also possible to dispose the optical position detection means 41A and 41B on both sides of the ultrasonic transducer 16. The transducer 16 may be located at a central portion between the optical position detection means 41A and 41B. The number of the optical position detection means is not limited to two, and the number may be two or more such as three.

Each of the optical position detection means 41A and 41B includes a light source 43 such as an LED for visualizing a surface of the inspection object 14, a light receiving section 44 comprising a light image pickup device for taking an image of the surface of the inspection object 14 irradiated with light by the light source 43, and a position detector 45 for detecting a moving direction and a moving distance of the inspection object 14 from the image data obtained by the light receiving section 44.

The light image pickup device constituting the light receiving section 44 comprises a CCD sensor or a CMOS sensor. A distance between the pair of optical position detection means 41A and 41B, and more concretely, between the light image pickup devices 44 and 44, is known and maintained constantly.

Position detection signals "a" detected by the position detectors 45 and 45 of the optical position detection device 17 are continuously captured by the position converting circuit 27, and the position converting circuit 27 continuously converts the moving distance of the central portion of the ultrasonic transducer 16, the moving direction and an inclination with respect to the moving direction from the two position detection signals "a".

The position converting circuit 27 outputs the converted moving distance, the moving direction and the inclination with respect to the moving direction to the display device 26, and the position converting circuit 27 then generates an imaging-start trigger signal whenever the moving amount of the central portion of the ultrasonic transducer 16 is varied by a preset constant value, and outputs the same to the signal generator 20.

The display device 26 receives, from the signal processor 24, an image information in which a plurality of image information sets generated in correspondence with the generation of the trigger signal are integrated. The display device 26 then couples both signals to each other based on received signal from the position converting circuit 27 (position conversion signal of the moving distance of the ultrasonic transducer 16, the moving direction and the inclination with respect to the moving direction), and can integrally display the internal inspection in the inspection object 14 when the ultrasonic probe device 12 assumes a necessary position as an ultrasonic wave image.

Figure 2:
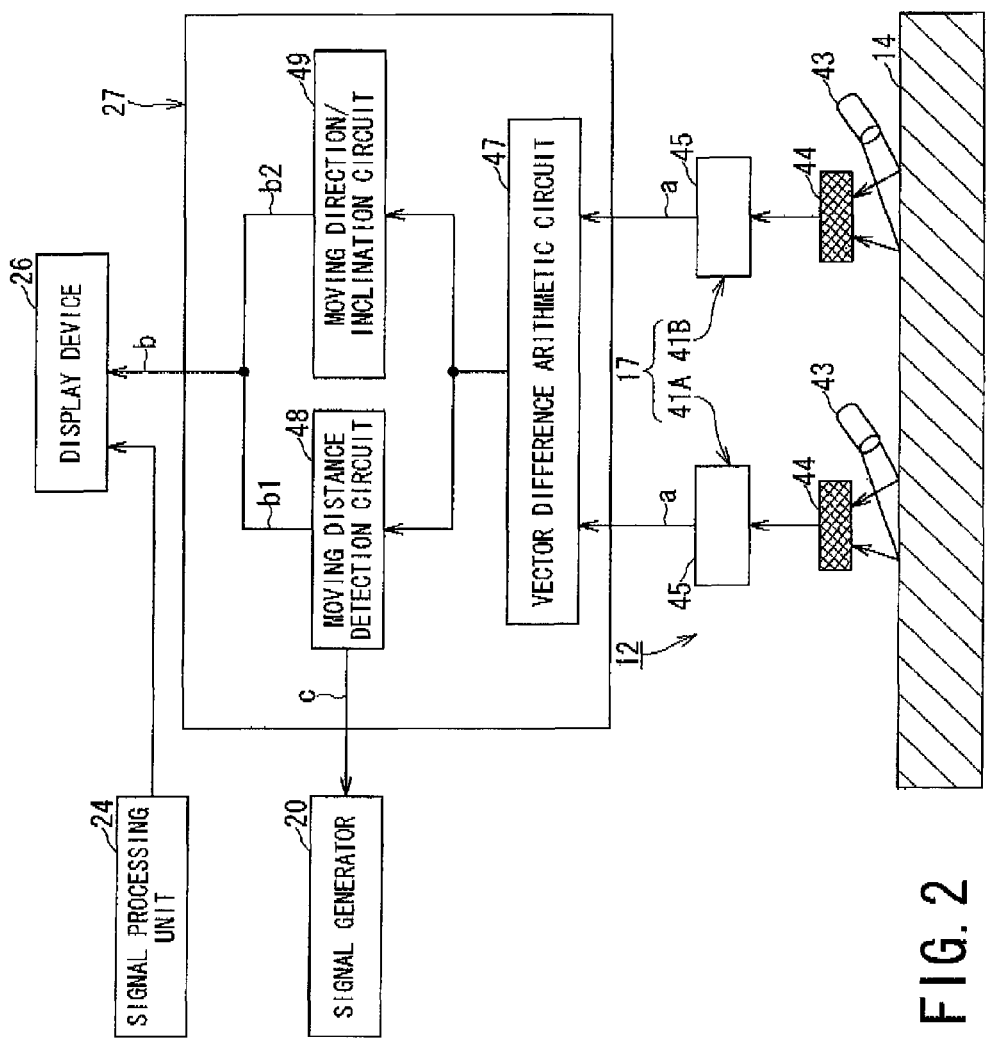
FIG. 2 is a block diagram of an ultrasonic probe provided for the ultrasonic inspection apparatus of FIG. 1.

More specifically, the position converting circuit 27 has a circuit structure as shown in FIG. 2. FIG. 2 shows an example in which the position converting circuit 27 is provided in the apparatus body 11, but the position converting circuit 27 may be provided in the probe holder 30 to constitute the ultrasonic probe 12. The ultrasonic probe 12 is provided with: a vector difference arithmetic circuit 47 for obtaining a difference between a vertical component and a horizontal component of two position detection informations which are outputted from the two position detectors 45 and 45 of the optical position detection device 17; a moving distance detection circuit 48 which detects a moving distance from the output (difference signal d) of the vector difference arithmetic circuit 47 and which outputs a trigger signal "c" to the signal generator 20 and outputs a position information signal b1 to the display device 26; and a moving direction/inclination detection circuit 49 which detects the moving direction and the inclination from the output (difference signal d) of the vector difference arithmetic circuit 47, and which outputs a position information signal b2 of the moving direction and the inclination to the display device 26.

The position converting circuit 27 detects position variation information of a moving amount from a reference position (initial position) of the ultrasonic transducer 16, a moving direction of the ultrasonic transducer 16, and an inclination thereof in accordance with the movement of the probe of the ultrasonic probe 12 and the variation of the positions of the light image pickup devices 44 and 44 of the optical position detection device 17. The position converting circuit 27 then outputs a position conversion signal "b" to the display device 26 and outputs an imaging-start trigger signal "c" to the signal generator 20.

More specifically, the position detectors 45 and 45 detect the positions of the two light image pickup devices 44 and 44 of the optical position detection device 17, and the detected positions are inputted to the vector difference arithmetic circuit 47 of the position converting circuit 48 periodically. The position detection information of the light image pickup devices 44 and 44 which is inputted to the vector difference arithmetic circuit 47 is composed of two components of X and Y in the horizontal direction and the vertical direction, respectively.

Figure 3A:
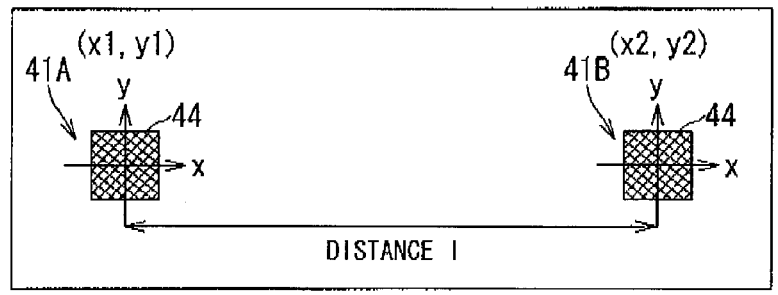
FIG. 3A and FIG. 3B are supplementary diagrams for explaining a probe moving amount from a positional relationship of a light image pickup device provided for the ultrasonic probe.
Figure 3B:
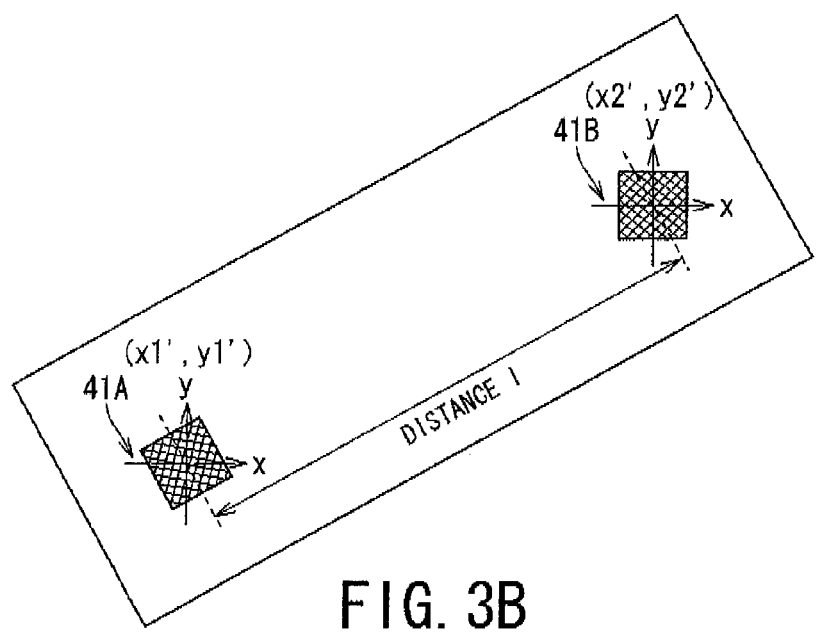

Here, X shows the horizontal direction and Y shows the vertical direction. The last input cycle positions of the two light image pickup devices 44 and 44 of the optical position detection device 17 are (x1, y1), (x2, y2) in the XY coordinate as shown in FIG. 3A, and the current input cycle positions thereof are (x1', y1'), (x2', y2') as shown in FIG. 3B. The distance between the two light image pickup devices 44 and 44 is 1, which has been known.

The vector difference arithmetic circuit 47 obtains a difference between the last value and the current value for the X component and Y component for each of the light image pickup devices 44 and 44, and the difference between the X component and Y component is expressed as follows:

A difference in X direction of the light receiving section 44 of the optical position detection means 41A: x1'−x1

A difference in Y direction of the light receiving section 44 of the optical position detection means 41A: y1'−y1

A difference in X direction of the light receiving section 44 of the optical position detection means 41B: x2'−x2

A difference in Y direction of the light receiving section 44 of the optical position detection means 41B: y2'−y2.

The moving distance detection circuit 48 calculates a moving distance based on the X component and Y component of the light image pickup devices 44 and 44 of the optical position detection means 41A and 41B. When the moving amount of a probe center position of the ultrasonic probe 12, i.e., the moving amount (probe moving amount, hereinafter) of the center position of the ultrasonic transducer 16 is to be detected, the probe moving amount is calculated in accordance with the following calculation method.

X component of probe moving amount;

$$\frac{(x_2' - x_2) + (x_1' + x_1)}{2}$$

Y component of probe moving amount;

$$\frac{(y_2' - y_2) + (y_1' + y_1)}{2}$$

The moving distance detection circuit 48 calculates the probe moving amount in synchronism with the input cycle of the vector difference arithmetic circuit 47, integrates the calculation results with respect to the XY components so as to obtain the moving distance from the probe movement-start time, and outputs the moving distance to the display device 26 as the probe moving amount. There will be provide various calculation methods of the probe moving amount, such as a method using polar coordinates in addition to the XY coordinates.

The trigger signal "c", which is output to the signal generator 20 from the moving distance detection circuit 48, is outputted when the probe moving amount reaches a preset trigger interval distance, i.e., a multiple of a distance such as 1 mm and 5 mm.

The moving direction/inclination detection circuit 49 of the position converting circuit 27 calculates a moving amount and an inclination of the ultrasonic probe device 12 based on the X direction component and the Y direction component of the two light image pickup devices 44 and 44 of the optical position detection device 17.

When the distance between centers of the two light image pickup devices 44 and 44 of the optical position detection device 17 is defined as "1", the moving direction of the ultrasonic probe 12 (probe moving direction, hereinafter) is expressed as follows:

Probe moving direction;

$$\mathrm{SIN}^{-1}\left\{\frac{(y_2' - y_2) + (y_1' + y_1)}{1}\right\}$$

In addition to the above calculation method of the probe moving direction, there are various calculation methods.

In the calculation of the probe moving direction, the angle of the moving direction in the vertical (Y) direction is 0° and the inclination at that time is also 0°. The moving direction/inclination detection circuit 49 calculates the probe moving direction in synchronism with the input cycle of the vector difference arithmetic circuit 47, and outputs the calculation result to the display device 26, which then displays the result on the display device 26.

In the ultrasonic inspection apparatus 10 shown in this embodiment, the ultrasonic probe 12 is electrically connected from the apparatus body 11 through the flexible signal cable 13, the ultrasonic inspection apparatus 10 is portable, and the ultrasonic probe 12 is accommodated integrally with the ultrasonic transducer 16 and the optical position detection device 17 in the palm-size probe holder 30. Therefore, the ultrasonic probe 12 can easily be manually operated along the surface of the inspection object 14.

When the ultrasonic probe 12 is manually operated, the optical position detection device 17 is not in contact with a surface of an inspection object 14. Therefore, maintenance operation or inspection of the optical position detection device 17 becomes unnecessary.

In the ultrasonic transducer 16, many piezoelectric elements 31 are arranged in the form of matrix or array to constitute the piezoelectric converter 32, and the non-contact optical position detection device 17 is integrally assembled with the ultrasonic transducer 16 in the probe holder 30 to constitute the ultrasonic probe device 12. Therefore, if an inspector manually operates the ultrasonic probe 12 on the surface of the inspection object 14, it is possible to easily carry out the ultrasonic flaw inspection of the internal state of the inspection object 14 at a field or site of manufacturing procedure.

Figure 4:
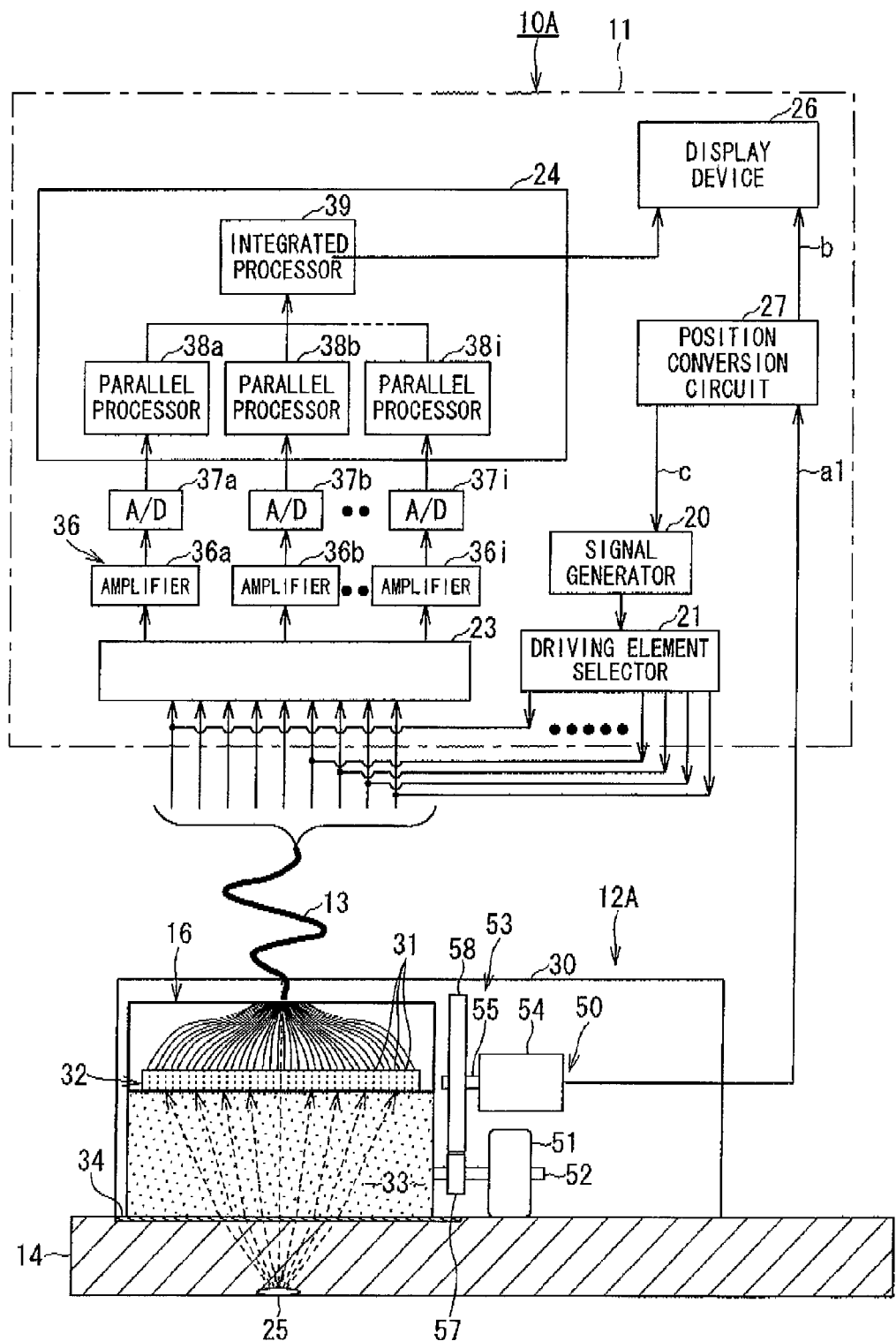
FIG. 4 is a block diagram showing a second embodiment of the ultrasonic inspection apparatus according to the present invention.

FIG. 4 is a schematic block diagram representing a second embodiment of the ultrasonic inspection apparatus according to the present invention.

According to an ultrasonic inspection apparatus 10A shown in this embodiment, a mechanical position detection device 50 is integrally assembled in a probe holder 30 of an ultrasonic probe 12. The other structure and function are the same as those of the ultrasonic inspection apparatus 10 shown in the first embodiment, so that the same elements are designated with the same symbols, and detailed explanation will be omitted herein.

According to the ultrasonic inspection apparatus 10A shown in the second embodiment, the ultrasonic transducer 16 and the mechanical position detection device 50 are integrally assembled in the probe holder 30 of the ultrasonic probe 12A.

The mechanical position detection device 50 rotatably supports a rotation shaft 52 having a wheel 51 on the side of the ultrasonic transducer 16, i.e., on the side of a shoe member 21 as an acoustic transmission medium. The rotation shaft 52 is connected to an input shaft 55 of an encoder 54 through a power transmission mechanism 53. A rotation amount of the wheel 51, i.e., a moving amount of the ultrasonic probe device 12A, is detected by the encoder 54, and the detection signal a1 is outputted to the position converting circuit 27.

The power transmission mechanism 53 is a gear mechanism comprising a pinion 57 which is provided on the rotation shaft 52 such that the pinion 57 rotates with the rotation shaft 52 in unison, and a gear 58 meshed with the pinion 57. The gear 58 rotates with the input shaft 55 of the encoder 54 in unison.

The ultrasonic inspection apparatus 10A shown in FIG. 4 is a portable inspection device, and the ultrasonic probe 12A connected to the apparatus body 11 through the flexible signal cable 13 is of palm-size and has the weight of 1 kg or less, more preferably, about 700 g.

According to the ultrasonic probe 12A, the ultrasonic transducer 16 and the mechanical position detection device 50 are integrally provided in the box-like probe holder 30.

The ultrasonic transducer 16 is integrally assembled with the mechanical position detection device 50.

The wheel 51 of the mechanical position detection device 50 grasps the probe holder 30 of the ultrasonic probe 12, and an inspector manually scans a surface of the inspection object 14 using the ultrasonic transducer 16 through the couplant 34 and the wheel 51 is thereby rotated in accordance with the moving amount, and the rotating amount is transmitted to the encoder 54 through the power transmission mechanism 53.

The encoder 54 outputs a pulse signal, in proportional to the number of rotations, to the position converting circuit 27, and the position converting circuit 27 converts the pulse signal into the moving amount of the ultrasonic probe 12A, i.e., of the ultrasonic transducer 16. The moving amount corresponds to the probe moving amount, the converted position signal b is sent to the display device 26, an imaging-start trigger signal "c" is generated every preset constant moving amount, and the signal is sent to the signal generator 20.

The display device 26 serves to couple the position signal "b" from the position converting circuit 27 and an ultrasonic wave image signal obtained by coupling the plurality of image information sets from the signal processor 24 to each other, and to display the same as integrated ultrasonic wave image at a timing based on the ultrasonic wave echo signal from the ultrasonic transducer 16 when a trigger signal received from the position converting circuit 27 is generated.

In the ultrasonic inspection apparatus 10A in this embodiment, the ultrasonic probe 12A is electrically connected through the flexible signal cable 13 from the apparatus body 11, and the ultrasonic inspection apparatus 10A is of a portable type. Further, in the ultrasonic probe 12A, the ultrasonic transducer 16 and the mechanical position detection device 50 are integrally accommodated in the probe holder 30. Therefore, it is possible to easily and manually operate the ultrasonic probe 12 along the surface of the inspection object 14.

In the ultrasonic transducer 16, many piezoelectric elements 31 are arranged in the form of matrix or array to constitute the piezoelectric converter 32. The mechanical position detection device 50 is integrally assembled with the ultrasonic transducer 16 in the probe holder 30 to constitute the ultrasonic probe 12A. Therefore, if an inspector manually operate the ultrasonic probe 12A on the surface of the inspection object 14 linearly, it is possible to easily carry out the ultrasonic flaw inspection of an internal state of the inspection object 14 at a field or a site of manufacturing procedure.

Figure 5:
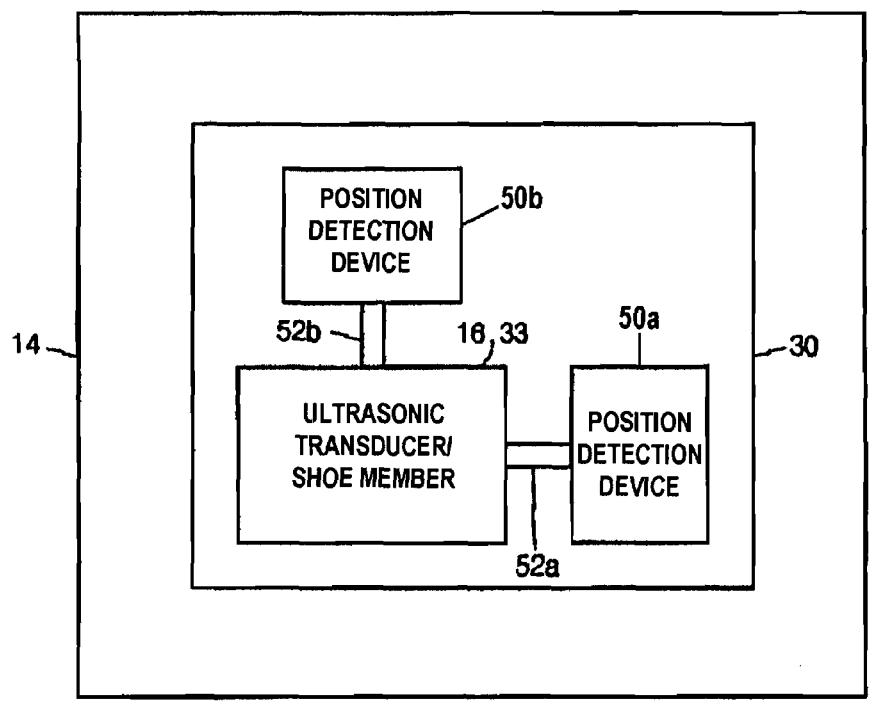
FIG. 5 is a block diagram of a top view of the ultrasonic probe holder.

In the ultrasonic inspection apparatus 10A shown in FIG. 4, to operate the ultrasonic probe 12A two dimensionally on a plane, two mechanical position detection devices 50 may be provided on the two intersecting side surfaces of the shoe member 33 of the ultrasonic transducer 16. For example, FIG. 5 illustrates a top view of the ultrasonic probe holder 30 configured to include two mechanical position detection devices 50a and 50b, respectively including rotation shafts 52a and 52b, provided on the two intersecting side surfaces of the shoe member 33 of the ultrasonic transducer 16.

In the embodiment of the present invention, the optical position detecting device or the mechanical position detection device is provided in the ultrasonic probe together with the ultrasonic transducer. However, it is possible to assemble a pole or a laser pointer provided in a mouse of a personal computer into the ultrasonic probe instead of the optical position detecting device or the mechanical position detection device, and also possible to constitute a position detection device capable of two dimensionally detecting a probe moving amount and a moving direction.

Although the optical or mechanical position detection device is assembled in the probe holder in the embodiment of the invention, the probe holder may be provided with the position detection device externally.

It is further to be noted that the present invention is not limited to the described embodiment and many other changes and modifications may be made without departing from the scopes of the appended claims.

What is claimed is:

1. An ultrasonic inspection apparatus comprising:
    an ultrasonic probe provided with an ultrasonic transducer including a plurality of piezoelectric elements and a position detection device;
    a drive element selector which is connected to the plurality of piezoelectric elements of the ultrasonic transducer provided and which selects a required piezoelectric element;
    a signal generator generating a drive signal for selecting the required piezoelectric element;
    a signal detection circuit which allows the piezoelectric element to transmit an ultrasonic wave to an inspection object through an acoustic transmission medium, which receives a reflection echo of the ultrasonic wave and which detects an electric signal of the reflection echo;
    a signal processor continuously generating three-dimensional imaging data inside of the inspection object by processing the electric signal of the detected reflection echo through a parallel arithmetic processing;
    a position converting circuit configured to output an imaging-start trigger signal to the signal generator in response to a position detection signal detected by the position detection device, the imaging-start trigger signal being a signal generated when the ultrasonic transducer is moved by more than a preset constant amount; and
    a display device displaying an imaging result in which a position detection signal of the ultrasonic transducer taken from the position converting circuit and a plurality of image data sets generated with the generation of the trigger signal and taken from the signal processor are integrally coupled to each other.

2. The ultrasonic inspection apparatus according to claim 1, wherein the ultrasonic probe is connected to an apparatus body of the ultrasonic inspection apparatus through a flexible signal cable, and the ultrasonic probe is integrally assembled with the ultrasonic transducer and the position detection device is a non-contact optical position detection device in a probe holder.

3. The ultrasonic inspection apparatus according to claim 2, wherein the optical position detecting device includes a pair of optical position detecting units, and each optical position detecting unit includes a light source which visualizes a surface of the inspection object, a light receiving section which receives a light reflected from the surface of the inspection object of an illumination light radiated from the light source, and a position detector which outputs a position detection signal detected by the light receiving section to the position converting circuit generating the image-start trigger signal.

4. The ultrasonic inspection apparatus according to claim 1, wherein the ultrasonic probe is connected to an apparatus body of the ultrasonic inspection apparatus, and the ultrasonic probe is integrally assembled with the ultrasonic transducer and a the position detection device, being a mechanical position detection device, in a probe holder.

5. The ultrasonic inspection apparatus according to claim 4, wherein the mechanical position detection device is provided on one side surface on the side of the ultrasonic transducer or two side surfaces which intersect with each other at right angles.

6. The ultrasonic inspection apparatus according to claim 4, wherein the mechanical position detection device is integrally provided on a side of the ultrasonic transducer, and the mechanical position detection device includes a wheel rolling on the surface of the inspection object and an encoder detecting a rotation amount of the wheel.

7. An ultrasonic probe connected to an ultrasonic inspection apparatus through a flexible signal cable, comprising:
    a box shaped probe holder;
    an ultrasonic transducer including a plurality of piezoelectric elements incorporated in the probe holder; and
    a position detection device integrally provided with the ultrasonic transducer and configured to detect the position thereof,
        wherein the ultrasonic transducer and the position detection device are integrally assembled in the probe holder, and the position detection device has an optical structure including at least a pair of optical position detectors, and the optical position detecting device is held in a non-contact state with respect to a surface of an inspection object when the probe holder is placed on the surface thereof in order to generate data for a continuous three-dimensional image of the inspection object.

8. The ultrasonic probe according to claim 7, wherein the optical position detecting device includes the at least a pair of optical position detectors, each of which includes a light source which visualizes a surface of an inspection object, a light receiving section which deflects a reflection light of an illumination light transmitted from the light source, and a position detector which outputs a position detection signal detected by the light receiving section to a position converting circuit.

* * * * *